US005412975A

United States Patent [19]
Raabe et al.

[11] Patent Number: 5,412,975
[45] Date of Patent: May 9, 1995

[54] UNIVERSAL INLET FOR AIRBORNE-PARTICLE SIZE-SELECTIVE SAMPLING

[75] Inventors: Otto G. Raabe; Stephen V. Teague, both of Davis, Calif.

[73] Assignee: The Regents of the University of California, Oakland, Calif.

[21] Appl. No.: 152,461

[22] Filed: Nov. 12, 1993

[51] Int. Cl.[6] .............. G01N 1/02

[52] U.S. Cl. .............. 73/28.04; 73/803.21

[58] Field of Search .............. 73/28.04–28.06, 73/863.21, 863.22; 55/270, 495, 510; 209/135, 139.1, 143

[56] References Cited

U.S. PATENT DOCUMENTS

| | | | |
|---|---|---|---|
| 3,070,990 | 1/1963 | Krinov | 73/28.04 |
| 3,518,815 | 7/1968 | McFarland . | |
| 3,983,743 | 10/1976 | Olin et al. . | |
| 4,038,057 | 7/1977 | Roth . | |
| 4,255,172 | 3/1981 | Smith . | |
| 4,321,822 | 3/1982 | Marple . | |
| 4,327,594 | 5/1982 | Nelson . | |
| 4,461,183 | 7/1984 | Wedding | 55/270 |
| 4,570,494 | 2/1986 | Dunn et al. . | |
| 4,640,140 | 2/1987 | Burghoffer et al. . | |

(List continued on next page.)

FOREIGN PATENT DOCUMENTS

| | | | |
|---|---|---|---|
| 913231 | 9/1946 | France | 73/28.04 |
| 469916 | 5/1975 | U.S.S.R. | 73/28.04 |

OTHER PUBLICATIONS

Raabe; "Aerosol Aerodynamic Size Conventions For Intertial Sampler Calibration"; 1976; APCA Journal, vol. 26, No. 9.
Raabe et al; "Calibration Studies of the Drum Impactor"; 1988; J. Aerosol Sco. Col 19, No. 2 pp. 183–195.
Bright et al; "New Portable Ambient Aerosol Sampler"; 1983; Am. Ind. Hyg. Assoc J. (44).

Buckley et al; "Calibration, Intersampler Comparison, and Field Application of a New PM–10 Personal Air–-Sampling Impactor"; Aerosol Science and Technology 14:380–387.

Burton et al; "Wide Range Aerosol Classifier: A Size Selective Sampler for Large Particles"; 1987; Aerosol Science and Rechnology 6:289–301.
Liu et al; "Aersol Sampling Inlets and Inhaleable Particles"; 1981; Atmosphere Environment vol. 15, pp. 589–600.

Marple et al; "High–Volume Impactor for Sampling Fine and Coarse Particles"; 1990; J. Air Waste Manage. Assoc. 40:762–767.

(List continued on next page.)

*Primary Examiner*—Robert Raevis
*Attorney, Agent, or Firm*—John P. O'Banion

[57] ABSTRACT

A universal airborne-particle size-selective inlet (10) for separating particles (82) larger than a cut size from particles (84) smaller than the cut size is disclosed. The larger particles (82) are separated by inertial collection as they are drawn into the apparatus (10) in an air stream (78) which exits jet orifices (46) aligned with collector holes (34) leading to closed stagnation chambers (24). The larger particles (82) pass through the collector holes (34) and into the stagnation chambers (24) where they remain. The smaller particles (84) are carried by the flowing airstream (78) that turns at, and passes by, the collector holes (34) to an external downstream small particle collection device. The apparatus (10) can be used for any flow rate or cut size based on aerodynamic conditions and dimensional ratios that relate the jet orifice (46) sizes to the sampling flow rate, the throat depth of the jet orifices (46), and the distance from the internal exit of the jet orifices (46) to the entrance of the collector holes (34).

15 Claims, 7 Drawing Sheets

U.S. PATENT DOCUMENTS

| | | |
|---|---|---|
| 4,640,768 | 2/1987 | Morbioli et al. ............ 209/139.1 |
| 4,725,294 | 2/1988 | Berger . |
| 4,740,220 | 4/1988 | Mark et al. . |
| 4,796,475 | 1/1989 | Marple . |
| 4,827,779 | 5/1989 | Marpel et al. . |
| 4,941,899 | 7/1990 | Liu ................................ 55/270 |

OTHER PUBLICATIONS

Marple et al; "Low Flow Rate Sharp Cut Impactors for Indoor Air Sampling: Design and Calibration"; 1987; JAPCA 37: 1303–1307.

McFarland et al; "A 10 um Cutpoint Size Selective Inlet For Hi-Vol. Samplers"; 1984; JAPCA 34: 544–547.

McFarland et al; "A New Cotton Dust Sampler for PM–10 Aerosol"; 1987; Am. Ind. Hyg. Assoc. J. 48 (3): 293–297.

McFarland et al; "A 10 um Cutpoint Ambient Aerosol Sampling Inlet"; 1982; Atmospheric Environmental vol. 16 No. 12 pp. 2959–2965.

Ortiz et al; "A 10–um Two–Stage Inlet for Sampling Indoor Aerosols"; 1985; APCA 35: 1057–1060.

Patashnick et al; "Continuous PM–10 Measurements Using the Tapered Element Oscillating Microbalance"; 1991; Air Waste Management Assoc. 41: 1079–1083.

Prodi et al; "An Inertial Spectrometer For Aerosol Particles"; 1979; Aerosol Sci. vol. 10 pp. 411–419.

Wedding et al; "A 10–um Cutpoint Inlet for the Dichotomous Sampler"; 1982; Enviro. Sci. Tech. 16, 602–606.

Wedding et al; "Wedding Ambient Aerosol Sampling Inlet for an Intermediate Flow Rate (4cfm) Sampler"; 1983; Envir. Sci. Tech. vol. 17, No. 7.

Wedding; "Ambient Aerosol Sampling. History, Present Thinking, and Proposed Inlet for Inhalable Particles"; 1982; Envir. Sco Tech., vol. 16, No. 3.

Wedding et al; "A Thoracic Particle Inlet For The High–Volume Sampler"; 1983; Atmospheric Environment. vol. 17, No. 6 pp. 1203–1204.

Wedding; "The Wedding Ambient Aerosol Sampling Inlet For The High Volume Sampler"; 1985; Atmospheric Environ. vol. 19, No. 3, pp. 535–538.

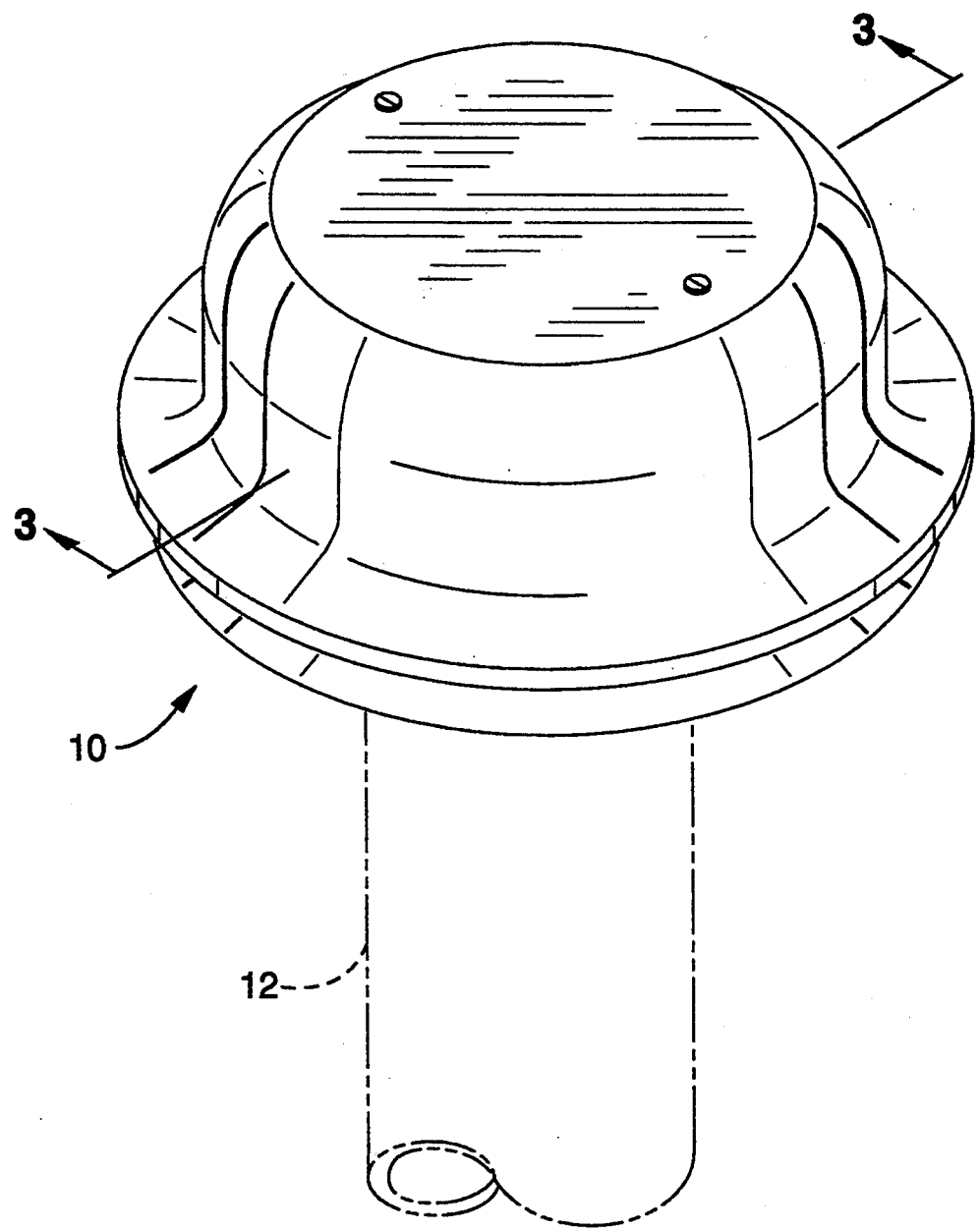
FIG. — 1

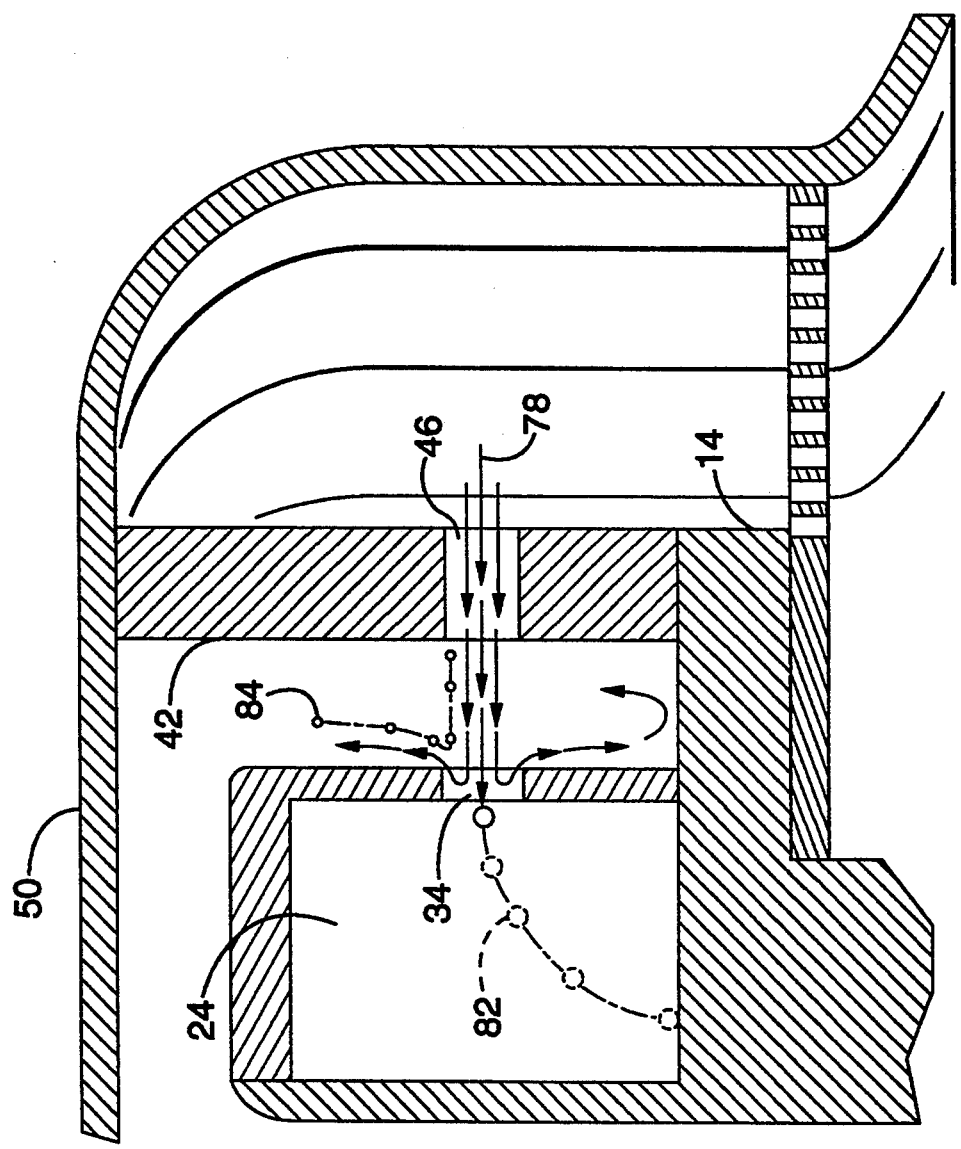
FIG. −7

UNIVERSAL INLET FOR AIRBORNE-PARTICLE SIZE-SELECTIVE SAMPLING

BACKGROUND OF THE INVENTION

1. Field of the Invention

This invention pertains generally to sampling airborne particulate matter, and more particularly to a universal inlet device for size-selective sampling of airborne particles which can be adjusted for different particle cut sizes and different sampling flow rates.

2. Description of the Background Art

Inhalable airborne particles are commonly sampled using size-selective air sampling inlets. Such inlets are generally designed to remove particles which are larger than a prescribed aerodynamic size, so that the particles collected by a downstream collector are limited in size to those which are inhalable by humans. Particles that pass through the inlet are typically collected on filters or by other means for analysis. The samples are then evaluated to determine possible heath risks from inhaling the particles.

For PM-10 sampling, government regulations require the air sampling instrument to be preceded by a sampling inlet that collects particles that tend to be larger than 10 micrometer in aerodynamic equivalent diameter following a prescribed efficiency standard (Title 40, Part 53 of the Code of Federal Regulations). A 50% collection efficiency is achieved for particles of aerodynamic diameter of 10±0.5 µm. The smaller particles can then pass to the subsequent collector, usually an efficient filter. A tolerance of 10% is applied to the total collected sample. The particles collected on the filter are retained as the PM-10 sample, and larger particles collected by the inlet are discarded when the inlet is cleaned.

Similar size-selective samplers are also used in industry for occupational and industrial hygiene and safety purposes. However, other cut sizes may be appropriate in those applications, such as the use of a cut size of 3.5 micrometer aerodynamic diameter for collecting respirable dust samples that describe particles that can penetrate to the deep lung if inhaled by people. In each of those cases, a tolerance of about 10% to 20% is usually applied to the ideal cut size to allow for normal variability in inlet performance.

Although there have been some specific sampling inlets designed previously, especially for the collection of PM-10 samples at about 1200 LPM, these inlets have been of relatively complex designs and have been flow-rate specific. That is, each of the existing designs can only be used to sample at one specified volumetric flow rate of air. If the PM-10 application requires a different flow rate or a different cut size is needed, existing designs are not directly usable.

Therefore, there is a need for a size-selective sampling inlet which can be scaled to meet different flow rates and cut size requirements. The present invention satisfies those needs, as well as others, and overcomes the deficiencies found in existing inlet designs.

SUMMARY OF THE INVENTION

The present invention generally comprises a size-selective airborne particle sampling apparatus which removes particles above a selected effective cutoff size so that only the smaller particles are collected for analysis. Sampling inlets for PM-10 sampling in accordance with the present invention are currently available for sampling flow rates ranging from 2.7 liters per minute to 21.7 liters per minute under conditions where wind speed passing the inlet ranges from zero to 24 km per hour. Higher flow rate inlets can be readily constructed using the design parameters of the present invention.

By way of example and not of limitation, the invention provides for inertial collection of larger particles which are drawn in an air stream exiting from a jet orifice and entering into a hole leading to a stagnation chamber by virtue of the particle inertia, and finally being collected by settling in the chamber. The smaller particles are carried by the flowing airstream that turns at the stagnation chamber opening and passes around the collector hole assembly to the downstream small particle collection device, such as a particle filter, for future analysis. Non-circular jet orifices and collector holes could also be used with appropriate characterization.

Several parallel identical jet orifices, collector holes, and stagnation chambers are operated together as a unit to achieve the desired sampling flow rate. The cut size can be readily calculated prior to assembly and set to any desired size by selection of the jet orifice diameter, number of orifices and collector holes, and sample flow rate.

As the larger particles are-thrown by their inertia into the collector hole that serves as the entrance to the stagnation chamber, their motion is rapidly slowed in the stagnant air in the chamber, and they eventually settle under the influence of gravity to the bottom surface of the chamber. Unlike inertial flow separator systems that might use branching flow paths, there is no net airflow into the stagnation chamber where the larger particles are collected by gravitational settling. The relatively large volume of the stagnation chamber eliminates the necessity for frequent cleaning of the collected material, although periodic cleaning will probably be desirable. Because the larger particles are collected in the stagnation chamber, they cannot be re-entrained into the airstream as would occur in systems that use impaction onto a surface as the method of collection. Also, the collected particles are not in contact with the incoming air stream, so they cannot interfere with the collection processes. These characteristics provide significant improvements over existing inlet designs.

An object of the invention is to provide a universal size-selective sampling inlet which can be set to any desired flow rate.

Another object of the invention is to provide a universal size-selective sampling inlet which can be set to any desired cut size.

Another object of the invention is to provide a sampling inlet wherein culled particles are not susceptible to being re-entrained into the air flow.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only:

FIG. 1 is a perspective assembled view of the apparatus of the present invention coupled to a suction tube shown in phantom.

FIG. 7 is an enlarged fragmentary view of FIG. 6 which diagrammatically shows air and particle flow through the apparatus.

DESCRIPTION OF THE PREFERRED EMBODIMENTS

Figure 2A:
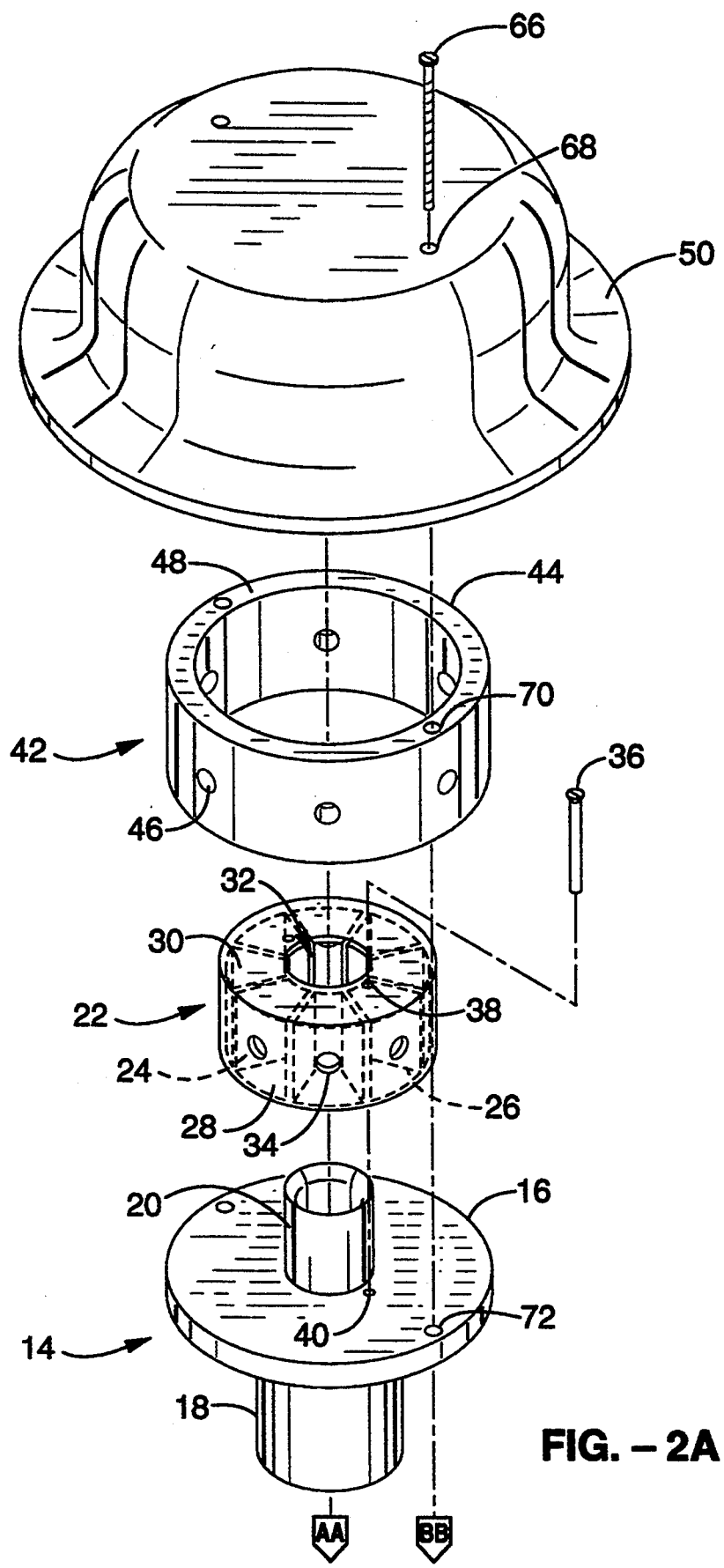
FIG. 2A through 2B is an exploded view of the apparatus shown in FIG. 1.
Figure 2B:
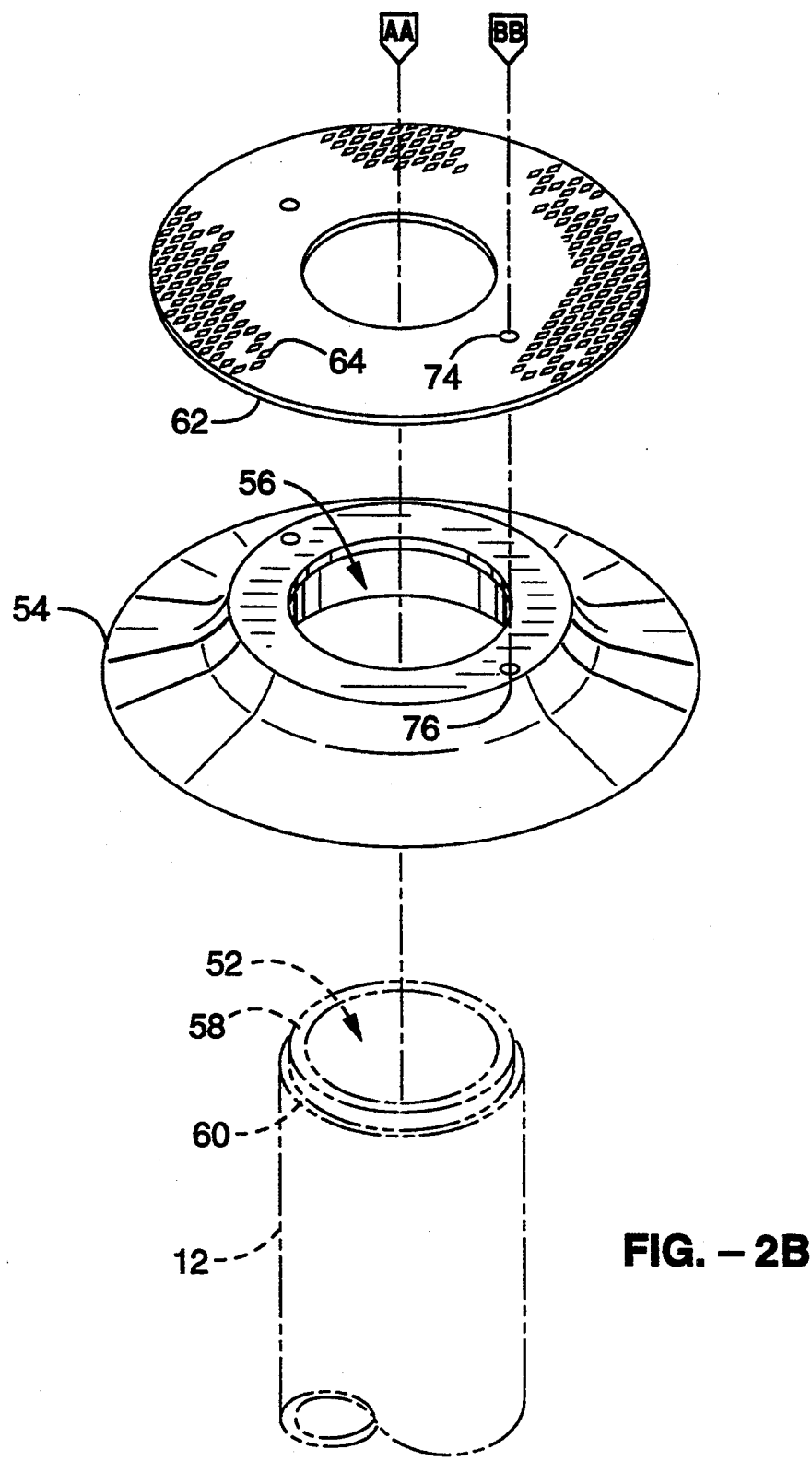
Figure 3:
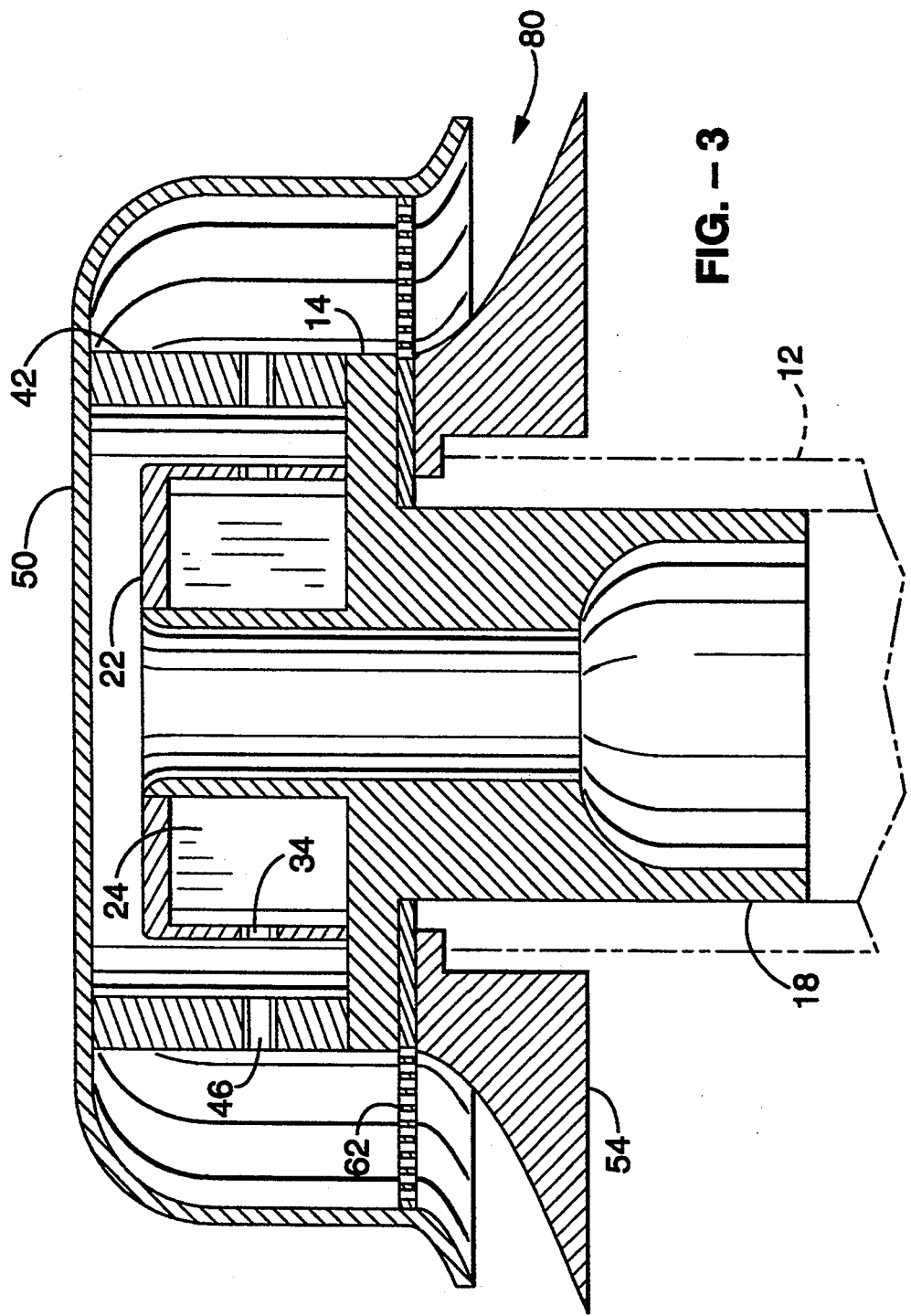
FIG. 3 is a cross-sectional view of the apparatus shown in FIG. 1 taken through line 3—3.
Figure 4:
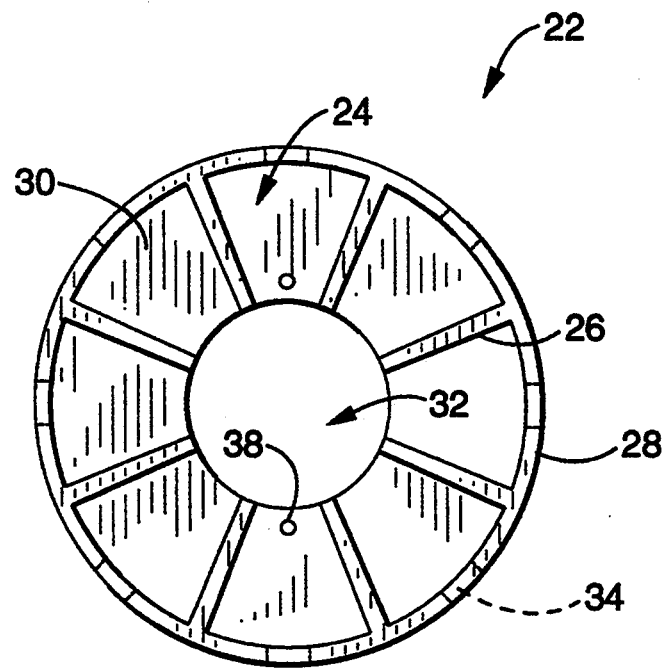
FIG. 4 is a top plan view of the stagnation chamber portion of the apparatus shown in FIG. 2A.
Figure 5:
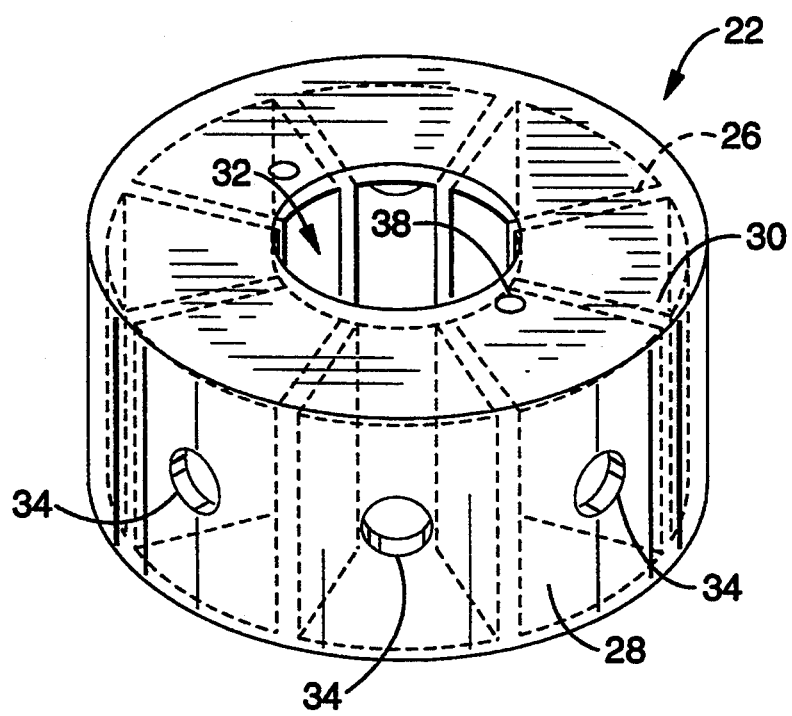
FIG. 5 is an enlarged perspective view of the stagnation chamber portion of the apparatus shown in FIG. 2A.

Referring more specifically to the drawings, for illustrative purposes the present invention is embodied in the apparatus which is generally shown in FIG. 1 through FIG. 7 where like reference numerals indicate like parts. It will be appreciated that the apparatus may vary as to configuration and as to details of the parts without departing from the basic concepts as disclosed herein.

The present invention generally comprises a single stage inertial particle chamber for collection of particles having aerodynamic diameters which are larger than the specified cut size. Referring to FIG. 1, a universal inlet 10 in accordance with the present invention is shown coupled to a suction tube 12 which in turn is coupled to a pump or other source of suction (not shown). The apparatus is designed of metal to prevent the buildup of electrostatic charge that might affect particle collection. Other materials, such as plastics, may be used if provision is made to minimize surface charging.

Referring to FIG. 2A and FIG. 3, the apparatus includes a base member 14 which is configured for coupling to a suction tube 12 or the like, which in turn is coupled to the filter pump or other source of suction (not shown). Base member 14 generally comprises an annular plate 16 through which an opening is coaxially disposed. As means of attachment to suction tube 12, a tubular coupling 18 having a coaxial through hole axially aligned with the opening in plate 16 extends downward from plate 16. Extending upward from plate 16 is a tubular retainer 20 having a coaxial through hole axially aligned with the hole in plate 16. In this way, air can pass through base member 14 by means of the openings extending through coupling 18, plate 16 and retainer 20.

A particle collector 22 rests on plate 16 for support. Referring also to FIG. 4 and FIG. 5, particle collector 22 includes a plurality of open compartments or stagnation chambers 24. These chambers are separated by a plurality of partitions 26 which are attached to and extend radially from a thin outer wall 28 toward the center of particle collector 22. As can be seen, each of the stagnation chambers 24 opens into a common central area. An upper wall 30 is provided to close the upper portion of stagnation chambers 24 by providing a seal against the upper edges of partitions 26. While a lower wall could also be provided, there is no such wall in the preferred embodiment. Instead, the upper surface of plate 16 functions as a lower wall for particle collector 22 by providing a seal against the lower edges of partitions 26. In this manner, stagnation chambers 24 can be easily cleansed of collected particles by removal of particle collector 22 from base member 14.

Upper wall 30 includes an air passage 32 which is coaxially disposed therein, and which fits over retainer 20 with tight engagement to form a seal. Particle collector 22 is not provided with a central inner wall since the outer surface of retainer 20 serves that function. Partitions 24 are sized such that they terminate against retainer 20 with a tight seal when particle collector 22 is installed. Alternatively, an inner wall could be included but such a wall would increase the difficulty of cleaning particles from stagnation chambers 24.

Particle collector 22 includes a plurality of orifices or collector holes 34, there being one collector hole 34 for each stagnation chamber 24. Each such collector hole 34 has an inlet which opens away from particle collector 22 and an outlet which opens into the stagnation chamber 24. As can be seen, therefore, once particle collector 22 is assembled in place, particle collector 22 includes a plurality of separate, sealed stagnation chambers which are accessible only through collector holes 34. The depth of each collector hole 34 is equal to the thickness of outer wall 28. Particle collector 22 is secured in placed by means of screws 36 which extend through holes 38 in upper wall 30 and engage threaded holes 40 in plate 16. Two such securing points are preferred.

A flow director 42, which is a generally annular ring having a diameter larger than that of particle collector 22, is positioned concentrically in relation to particle collector 22 and rests on plate 16. The spacing between the inner surface of wall 44 of flow director 42 establishes a flow area between flow director 42 and particle collector 22. Flow director 42 includes a plurality of jet orifices or flow holes 46 which are equal in number to collector holes 34, and which are axially aligned with collector holes 34. Each flow hole 34 has an inlet which opens away from flow director 42 and an outlet which opens into the flow area between flow director 42 and particle collector 22. The thickness of wall 44 is equal to the depth or "throat length" of the flow holes 34. Also, when flow director 42 rests on plate 16, its upper edge 48 extends above upper wall 30 of particle collector 22.

A flared cap 50 shrouds the assembly thus far described. The inner surface of cap 50 rests on upper edge 48 of flow director 42 and forms a tight seal.

Referring also to FIG. 2B, suction tube coupling 18 is of such a diameter that it fits into hole 52 in suction tube 12 and is secured by means of frictional engagement. A flared skirt 54, having a hole 56 positioned coaxially therein, fits over the neck 58 of suction tube 12 and rests on shoulder 60. A screen 62 rests on the upper surface skirt 54, and includes a coaxially positioned hole 64 through which neck 58 also extends. In the preferred embodiment, screen 62 is a flat, perforated plate having approximately 40% of open area. Those skilled in the art will appreciate that the size of the openings in screen 62 must be sufficiently large to pass the particles to be collected, but sufficiently small to prevent insects and debris from entering the apparatus.

The entire assembly is secured as a unit by means of screws 66, of which there are preferably at least two, which extend through holes 68 in cap 50, holes 70 in flow director 42, holes 72 in base member 18, and holes 74 in screen, and engage threaded holes 76 in skirt 54.

Figure 6:
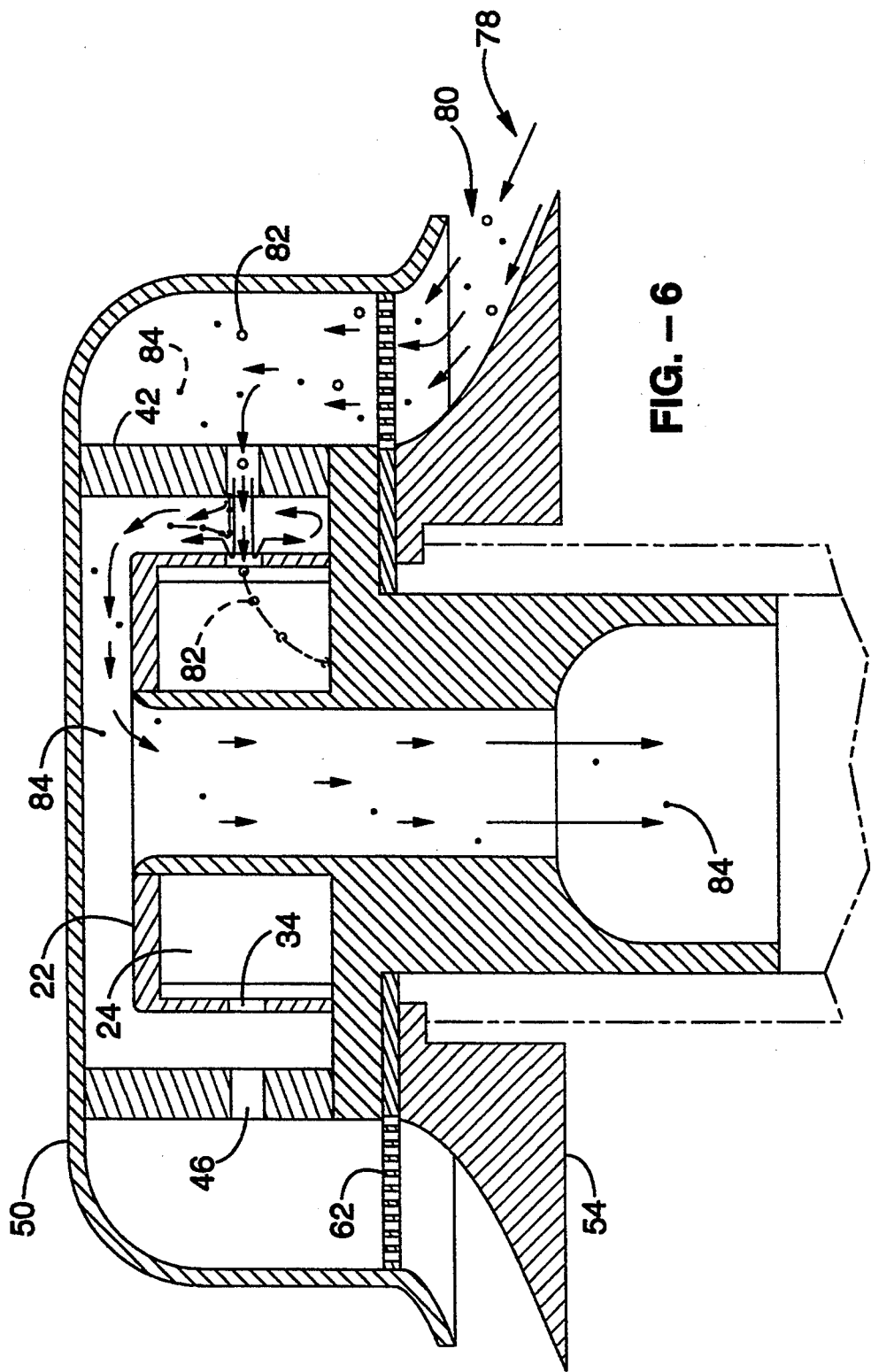
FIG. 6 is an enlarged view of FIG. 3 which diagrammatically shows air and particle flow through the apparatus.

Referring to FIG. 6 and FIG. 7, air 78 is sampled through the annular slit 80 formed between cap 50 and skirt 54. This flow is induced by suction or vacuum applied at the base of suction tube 12, which is a vertical cylindrical tube leading to the sample collector (not shown) positioned below the apparatus. After entering the annular slit 80, the air 78 passes through screen 62 to collect debris or insects that would otherwise enter the apparatus. The air 78 then passes through one or more of the several flow holes 46 which serve as jet orifices. Air 78 exits the flow holes 46 as jets of air which are directed toward the collector holes 34. It can be seen that collector holes 34 are a matched series of blind holes axially aligned with flow holes 46 and which serve as a stagnation obstacles in particle collector 22. The air 78 partially enters the inlet portion of these blind holes but cannot enter stagnation chambers 24. The air 78 then turns upward around this stagnation obstacle, passes through the flow area between flow director 42 and particle collector 22, passes downward through the center of retainer 20, plate 16 and suction coupling 18, and then passes-into suction tube 12 which carries it to the filter or other sample collection system. The air 78 can only partially enter the inlet portion of collector holes 34 before turning a right angle because particle collector 22 is a closed system. However, the large particles 82, which are above the cut size, pass through collector holes 34 by their inertia and are accumulated in stagnation chambers 24. Once inside stagnation chambers 24, the large particles 82 fall downward under the influence of gravity. The small particles 84, however, are carried in the stream of air 78 through the center of the apparatus and through suction tube 12 to the collection filter.

Several important characteristics can be noted at this point. First, the flow holes 46 function as jet orifices which direct the flow of air 78 and large particles 82 toward collector holes 34. As the throat length (hole depth) of flow holes 46 increases, the precision of separation increases. Second, when it reaches the stagnation obstacle (blind collector holes 34), the air 78 essentially makes a right angle turn. This turn is generally upward in the direction of the flow path to the external collection filter, but could be downward as is depicted in FIG. 6 and FIG. 7. If the air 78 turns downward as shown, it will thereafter turn upward because it cannot travel further in the downward direction due to the obstacle presented by plate 16 of base member 14. Third, small particles 84 are swept along with air 78 and, since their inertia is small compared to large particles 82, small particles 84 do not enter collector holes 34.

The particle cut-size for any size hole arrangement and flow rate can be precisely calculated using the appropriate Stokes number from classical particle mechanics in an air stream that changes direction. The Stokes number is a dimensionless parameter that can be used with simple equations to derive the cut size at any flow rate and air jet size combination. This invention could also be arranged with a rectangular or slit jet and collector opening using established theory of particle mechanics for rectangular jets.

The collection efficiency of the invention depends upon several geometric and dynamic factors including: (a) particle size (the diameter, D, for a spherical particle); (b) the particle physical density, $\rho$; (c) the particle shape; (d) the Cunningham slip correction, C(D) (important for submicrometer particles); (e) the linear velocity of the air stream at the outlet of each flow hole 46 (usually described by a hypothetical average, $u_o$, equal to the volumetric flow rate, $Q_o$, divided by the cross-sectional area of the flow hole 46); (f) the dynamic characteristics of the jet air flow (conveniently described by the air flow Reynolds' number, Re, at the outlet of each flow hole 46); (g) the dynamic viscosity of the air, $\eta$; (h) the size and shape of each flow hole 46 (conveniently described by the outlet diameter, W, for cylindrical holes); (i) the distance, S, from the outlet of each flow hole 46 to the inlet of each collector hole 34, and (j) the depth or throat length, T, of each flow hole 46.

It is assumed that a single aerosol particle exits an orifice at a velocity, $v_p$, equal to the gas velocity, $v_g$, and that they are equal to the maximum average velocity of the airstream jet, $u_o$. As the airstream turns to avoid the collector, the particle decelerates in the direction of the collector under a drag force (F=ma) given by Stokes' law:

$$\frac{v_g - v_p}{B} = m \frac{dv_p}{dt} \qquad (1)$$

where B is the particle mobility, m is the particle mass, and t is time. Based upon the principles of physical and dynamic similarity and dimensional analysis, the behavior of the particle and its associated collection probability or efficiency can be expressed in non-dimensionalized general form by normalizing the various factors in the equation of motion in the direction perpendicular to the collector so that Equation (1) is multiplied by $W/2u_o^2$ and the dimensionless $t^* = 2u_o t/W$ and velocities $v_g^* = v_g/u_o$ and $v_p^* = v_p/u_o$ are substituted to yield:

$$v_g^* - v_p^* = (Stk) \frac{dv_p^*}{dt^*} \qquad (2)$$

where the mass of the particle has been replaced by the dimensionless Stokes' number as defined by:

$$Stk = \frac{2mBu_o}{W} = \frac{u_o \rho^* D_{ar}^2}{9\eta W} \qquad (3)$$

where $\eta$ is the dynamic viscosity and $u_o$ is the calculated average velocity of the air stream at the jet exit, $\rho^*$ is a standard reference physical density equal to one g/cm$^3$ used to define the aerodynamic diameter, W is the jet diameter (for cylindrical jets) and $D_{ar}$ is the aerodynamic resistance diameter of particle as defined by:

$$D_{ar} = \frac{D\sqrt{\rho \, C(D)}}{\sqrt{\rho^*}} = \frac{D_e \sqrt{\rho \, C(D_s)}}{\sqrt{\kappa \rho^*}} \qquad (4)$$

where $\rho$ is the physical density of a spherical particle of physical diameter D and C(D) is the Cunningham slip correction used to correct Stokes' law of particle drag for violation of the no-slip boundary condition between the particle and air molecules. The right hand relationship is for non-spherical particles where $D_e$ refers to the equivalent volume diameter, K the dynamic shape factor, and $D_s$ to the equivalent slip diameter of a non-spherical particle.

The slip correction can be calculated for spherical solid aerosol particles in air using:

$$C(Kn) = 1 + A\,Kn \quad (5)$$

with Kn the Knudsen number equal to $2\lambda/D$, where $\lambda$ is the gas molecule mean free path, and $$A = \alpha + \beta \exp(-\xi/Kn) \quad (6)$$

where $\alpha$, $\beta$, and $\xi$ are characteristic parameters whose values for solid particles are 1.142, 0.558, and 0.999, respectively.

The particle aerodynamic equivalent diameter, $D_{ae}$, defined as the unit density (1 g/cm$^3$) sphere having the same settling velocity as a specified aerosol particle, is related to $D_{ar}$ by:

$$D_{ae} = \frac{D_{ar}}{\sqrt{C(D_{ae})}} \quad (7)$$

where $C(D_{ae})$ is the slip correction appropriate for a spherical particle of physical diameter equal to $D_{ae}$.

An efficiency function given as a function of Stokes' number will apply for all sizes of particles and air jet orifices as long as physical and dynamic similarity is maintained, i.e, T/W, S/W, and Re are fixed. The efficiency function can be described in terms of the effective cutoff aerodynamic diameter ($ECD_{ae}$ or $ECD_{ar}$), defined as the particle size (with corresponding Stokes' number) having a 50% collection efficiency. When the Stk for 50% collection efficiency into a hole is known, the $ECD_{ar}$ can be calculated from:

$$ECD_{ar}=\sqrt{\frac{9\ \eta\ WStk}{u_o\rho^*}} \quad (8)$$

and $ECD_{ae}$ can be calculated from $ECD_{ar}$ for the local pressure and temperature conditions. In order to utilize this non-dimensional analysis for sonic and near sonic jets, a discharge coefficient, c, is used to correct the cross sectional area of the jet orifice for the effect of flow stream contraction in choked or partially choked flow for calculating the jet velocity, $u_o$; therefore, the square root of c was multiplied by W to yield the effective jet diameter for Equation 8.

The mean free path of air molecules in the outlet jet flow is given by:

$$\lambda_o=\lambda^*\left(\frac{T_o}{T^*}\right)\left(\frac{P^*}{P_o}\right)\left(\frac{1+\frac{S^*}{T^*}}{1+\frac{S^*}{T_o}}\right) \quad (9)$$

where $P_o$ is the static pressure and $T_o$ is the absolute temperature of the air, $S^*$ is the Sutherland correction equal to 110.4° K., $P^*=101.3$ kPa and $T^*=296.15$° K. at which conditions $\lambda^*=0.0673$ $\mu$m.

Likewise, the dynamic viscosity of the air can be calculated from:

$$\eta_o=\eta^*\left(\frac{T_o}{296.15}\right)^{1.5}\left(\frac{296.15+S^*}{T_o+S^*}\right) \quad (10)$$

where $\eta^*$ is the viscosity of air at 23° C. (296.15° K.) equal to $1.832\times10^{-5}$ kg m$^{-1}$ s$^{-1}$. We have determined that a Stokes' number of 0.2 characterizes our design and provides the necessary solution to equation 8 above. Hence, the cutoff size for apparatus can be readily calculated prior to assembly and set to any desired size by selection of the jet orifice diameter, number of orifice collectors, and sample flow rate using the above equations.

The following tables show the relationship of various design parameters for three different inlets in accordance with the present invention. Note that in each table the number of flow holes 42 and collector holes 34 is eight. Other numbers, such as sixteen, could be used for higher flow rates if desired. In practice, the total flow rate would first be specified. Then the number of flow holes would be selected and, from the flow rate and number of flow holes, the flow hole diameter would be calculated to provide the required effective cutoff aerodynamic diameter. Then, the remaining parameters would be determined based on the flow hole diameter. There are certain boundaries on this selection, however. First, the flow velocity should preferably not exceed 30% of the speed of sound. Second, for a Stk=0.2, the Re should be between 300 and 5000. Third, the pressure drop through the flow holes should be small or negligible.

TABLE 1

| Cut Size = 2.5 $\mu$m; Flow Rate = 10 LPM | |
|---|---|
| Number of Holes | 8 |
| Flow Holes | |
| Diameter (W) | 0.172 cm |
| Depth (T) | 0.380 cm |
| Flow Per Hole | 1.25 liters per minute |
| Flow velocity | 897 cm/s |
| Reynolds Number (Re) | 991 |
| Pressure Drop | 0.5 cm $H_2O$ |
| Collector Holes | |
| Diameter | 0.19 cm |
| Depth | 0.10 cm |
| Hole to Hole Distance (S) (flow to collector) | 0.344 cm |

TABLE 2

| Cut Size = 10.0 $\mu$m; Flow Rate = 10 LPM | |
|---|---|
| Number of Holes | 8 |
| Flow Holes | |
| Diameter (W) | 0.43 cm |
| Depth (T) | 0.43 cm |
| Flow Per Hole | 1.25 liters per minute |
| Flow velocity | 100 cm/s |
| Reynolds Number (Re) | 396 |
| Pressure Drop | 0.1 cm $H_2O$ |
| Collector Holes | |
| Diameter | 0.46 cm |
| Depth | 0.15 cm |
| Hole to Hole Distance (S) (flow to collector) | 0.43 cm |

TABLE 3

| Cut Size = 10.0 $\mu$m; Flow Rate = 23 LPM | |
|---|---|
| Number of Holes | 8 |
| Flow Holes | |
| Diameter (W) | 0.57 cm |
| Depth (T) | 0.57 cm |
| Flow Per Hole | 2.88 liters per minute |
| Flow velocity | 188 cm/s |
| Reynolds Number (Re) | 688 |
| Pressure Drop | 0.1 cm $H_2O$ |

TABLE 3-continued Cut Size = 10.0 μm; Flow Rate = 23 LPM

| Collector Holes | |
| --- | --- |
| Diameter | 0.61 cm |
| Depth | 0.15 cm |
| Hole to Hole Distance (S) (flow to collector) | 0.57 cm |

In connection with these tables, several items should be noted. First, the spacing between the flow holes 42 and collector holes 34 should fall within the range of approximately 1 to 2 times the diameter of the flow holes 42 (S/W=1 to 2). In order for the foregoing relationships to hold, the S/W should not be less than 1. Additionally, the throat depth, T, should fall in the range of approximately 1 to 5 times the diameter of the flow holes 42 (T/W=1 to 5). This range will ensure that the air flowing through the outlet of flow holes 42 will exit as a jet which directs the larger particles 82 toward collector holes 34. Also, it is preferred that the diameter of the collector holes 34 be approximately 10% greater than the diameter of the flow holes 42. Lastly, the thickness of the outer wall of particle collector 22 should be less than approximately one-half of the diameter of the collector holes 34. These last two parameters will ensure that the larger particles 82 will enter collector holes 34 without being caught on the lower edge of the holes and will not be re-entrained into the air 78.

Accordingly, it will be seen that this invention provides a highly efficient inlet for size-selective sampling, provides an inlet design which can be used at different flow rates and cut sizes, and which prevents re-entrainment of particles commonly found in impaction type collectors. Although the description above contains many specificities, these should not be construed as limiting the scope of the invention but as merely providing illustrations of some of the presently preferred embodiments of this invention. Thus the scope of this invention should be determined by the appended claims and their legal equivalents.

We claim:

1. A size-selective particle sampling inlet apparatus, comprising:
    (a) flow director means for receiving a stream of air containing particles having aerodynamic equivalent diameters larger and smaller than a specified cut size and for converting said particle containing stream of air into a jet stream, said flow director means comprising a ring having a plurality of flow orifices;
    (b) particle collector means for receiving said particles having aerodynamic equivalent diameters larger than said cut size, said particle collector means including an outer wall having a plurality of collector orifices, each of said collector orifices spaced apart from and axially aligned with a corresponding one of said flow orifices; and
    (c) stagnation chamber means for containing said received particles.

2. An apparatus as recited in claim 1, wherein said particle collector means is positioned coaxially with said flow director means.

3. An apparatus as recited in claim 1, wherein said stagnation chamber means comprises a plurality of sealed chambers and wherein said collector orifices open into said sealed chambers.

4. An apparatus as recited in claim 1, further comprising inlet screen means for receiving a flow of air containing airborne particles to be sampled and filtering insects and debris from said flow of air and airborne particles.

5. An apparatus as recited in claim 1, further comprising flow passage means for conducting said air and airborne particles having an aerodynamic equivalent diameter smaller than said cut size around said particle collector means and to an external downstream sample collector system.

6. A particle collection apparatus, comprising:
    (a) flow director means for directing a flow of air containing airborne particles through a plurality of jet orifices and for imparting flow velocity to said air and said airborne particles;
    (b) stagnation obstacle means for separating airborne particles having an aerodynamic equivalent diameter larger than a specified cut size from airborne particles having an aerodynamic equivalent diameter smaller than said cut size, said stagnation obstacle means including a plurality of blind collector openings, each of said blind collector openings spaced apart from and axially aligned with a corresponding one of said jet orifices, each of said blind collector openings providing passage through said stagnation obstacle means into said stagnation collector chamber means; and
    (c) stagnation collection chamber means for receiving and containing said airborne particles having an aerodynamic equivalent diameter larger than said cut size.

7. An apparatus as recited in claim 6, wherein said stagnation obstacle means is positioned coaxially with said flow director means.

8. An apparatus as recited in claim 6, wherein said stagnation collection chamber means is sealed and air exiting said jet orifices is unable to pass through said blind collector openings, and wherein said received airborne particles pass through said blind collector openings by inertial force.

9. An apparatus as recited in claim 6, further comprising inlet screen means for receiving said flow of air containing airborne particles to be sampled and filtering insects and debris from said flow of air and airborne particles.

10. An apparatus as recited in claim 6, further comprising flow passage means for conducting said air and airborne particles having an aerodynamic equivalent diameter smaller than said cut size around said stagnation obstacle means and to an external downstream sample collector system.

11. A particle separation apparatus, comprising:
    (a) a base member;
    (b) an annular ring, said annular ring coupled to said base member, said annular ring having a coaxially disposed opening, said annular ring including a plurality of radially disposed flow orifices; and
    (c) a generally cylindrical particle collector, said particle collector coupled to said base, said particle collector coaxially disposed within said opening in said annular ring, said particle collector including a plurality of stagnation chambers, said particle collector including a plurality of radially disposed collector orifices, each said collector orifice opening into a corresponding one of said stagnation chambers, each said collector orifice spaced apart from and axially aligned with a corresponding one of said flow orifices.

12. An apparatus as recited in claim 11, wherein each said stagnation chamber is sealed against air flow.

13. An apparatus as recited in claim 11, further comprising inlet screen means for receiving a flow of air containing airborne particles to be sampled and filtering insect and debris from said flow of air and airborne particles.

14. An apparatus as recited in claim 13, wherein said received airborne particles pass through said collector orifices by inertial force.

15. An apparatus as recited in claim 11, further comprising flow passage means for conducting air and airborne particles having an aerodynamic equivalent diameter smaller than a specified cut size around said particle collector and to an external downstream sample collector system.

* * * * *